US008617162B2

(12) United States Patent
Steinwachs et al.

(10) Patent No.: US 8,617,162 B2
(45) Date of Patent: Dec. 31, 2013

(54) DEVICE FOR PUNCHING OUT TISSUE AREAS FROM BONE

(75) Inventors: Matthias Steinwachs, Herrliberg (CH); Sascha Berberich, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 1451 days.

(21) Appl. No.: 11/566,037

(22) Filed: Dec. 1, 2006

(65) Prior Publication Data

US 2007/0173877 A1 Jul. 26, 2007

Related U.S. Application Data

(63) Continuation of application No. PCT/EP2005/005624, filed on May 25, 2005.

(30) Foreign Application Priority Data

Jun. 3, 2004 (DE) .......................... 10 2004 028 429

(51) Int. Cl.
 *A61B 17/00* (2006.01)
 *A61B 17/14* (2006.01)
 *A61B 17/32* (2006.01)

(52) U.S. Cl.
 USPC ............................ 606/79; 606/86 R; 606/184

(58) Field of Classification Search
 USPC ............. 606/79–85, 179, 181–186; 600/562, 600/564–568, 582–584, 587; 30/301, 30/314–316, 358
 See application file for complete search history.

(56) References Cited

U.S. PATENT DOCUMENTS

| 4,696,308 A * | 9/1987 | Meller et al. ................... 600/567 |
| 4,782,833 A * | 11/1988 | Einhorn et al. .................. 606/80 |
| 5,062,845 A * | 11/1991 | Kuslich et al. .................. 606/80 |
| 5,331,972 A * | 7/1994 | Wadhwani et al. ........... 600/567 |
| 5,586,989 A * | 12/1996 | Bray, Jr. ........................ 606/160 |
| 5,676,545 A * | 10/1997 | Jones ............................ 433/165 |
| 5,782,835 A * | 7/1998 | Hart et al. ....................... 606/79 |
| 6,063,088 A * | 5/2000 | Winslow ..................... 606/86 A |
| 6,110,127 A * | 8/2000 | Suzuki .......................... 600/565 |
| 6,270,498 B1 * | 8/2001 | Michelson ..................... 606/914 |
| 6,436,098 B1 * | 8/2002 | Michelson .................. 606/86 A |
| 6,451,023 B1 * | 9/2002 | Salazar et al. .............. 606/86 R |
| 6,761,726 B1 * | 7/2004 | Findlay et al. ................. 606/182 |
| 6,916,322 B2 * | 7/2005 | Jesch .............................. 606/80 |
| 7,063,711 B1 * | 6/2006 | Loshakove et al. ........... 606/153 |
| 2002/0099382 A1 * | 7/2002 | Salazar et al. .................. 606/86 |
| 2003/0022132 A1 * | 1/2003 | Jesch ............................ 433/165 |
| 2004/0034437 A1 | 2/2004 | Schmieding ................. 623/908 |
| 2004/0220497 A1 * | 11/2004 | Findlay et al. ................ 600/562 |
| 2005/0090830 A1 * | 4/2005 | Salazar et al. .................. 606/80 |
| 2006/0241517 A1 * | 10/2006 | Fowler et al. ................. 600/583 |
| 2007/0123891 A1 * | 5/2007 | Ries et al. ....................... 606/80 |

OTHER PUBLICATIONS

International Preliminary Report on Patentability & Written Opinion, Dec. 28, 2006, 6 pages.
International Search Report; Jul. 29, 2005; 3 pages.
Behrens, P. et al.;"ACT und Tissue Engineering," DGU—Mitteilungen und Nachrichten 45/2002 1; 8 pages.
Advertising Literature; Cartilage Regeneration System; Ars Arthro AG, The Art of Mobility; 12 pages.

* cited by examiner

*Primary Examiner* — Matthew Lawson
(74) *Attorney, Agent, or Firm* — St. Onge Steward Johnston & Reens LLC

(57) ABSTRACT

A device for punching out tissue areas from bone has a blade whose circumferential cutting edge corresponds to the contour of a tissue area that is to be punched out. The blade is composed of a plurality of blade segments that are each movable in an axial direction counter to the force of a spring.

11 Claims, 4 Drawing Sheets

DEVICE FOR PUNCHING OUT TISSUE AREAS FROM BONE

BACKGROUND OF THE INVENTION

The invention relates to a device for punching out tissue areas from bone, with a blade whose circumferential cutting edge corresponds to the contour of a tissue area that is to be punched out.

Tissue punches of this kind, also called cartilage punches, are sold by the company Ars Arthro AG, 73728 Esslingen, Germany.

Such punches are used, for example, in autologous chondrocyte transplantation (ACT), see DGU—Mitteilungen und Nachrichten 45/2002 1, "ACT und Tissue Engineering" under the auspices of the DGU and DGOOC.

The hyaline articular cartilage of humans varies in thickness depending on topography. In the area of the patella, it can reach a layer thickness of 7 to 8 mm. Since the articular cartilage has no direct vessel or nerve attachments, it is nourished mainly through diffusion from the synovial fluid of the intraarticular space. The crosslinking of various matrix components to form the ground substance of the cartilage permits mechanical damping and almost frictionless sliding of the articular surfaces. At the cellular level, there is a complex structure of cartilage cells (chondrocytes), collagen fibres and proteoglycans. The healthy hyaline cartilage of an adult is able to tolerate loads that can amount to a multiple of the body's weight.

Damage to the articular cartilage represents a major problem in routine traumatology and orthopedics. The limited healing capacity of the hyaline cartilage has long been recognized and is mainly due to its particular structure and anatomy.

Damage to the articular surface, above all in the area of the load-bearing zone of the sliding surface of the joint, therefore entails increased risk of substantial joint damage in the sense of premature arthrosis. Known methods for biological reconstruction of full-thickness cartilage damage are in most cases suitable only for small to medium-sized defects. In cases of full-thickness cartilage damage, especially in the area of the knee joint, with a defect covering more than about 4 $cm^2$, autologous chondrocyte transplantation (ACT) is therefore gaining increased clinical application.

In this method, a specimen of cartilage is removed arthroscopically from a non-supporting part of the joint. The cartilage cells from the biopsy specimen are isolated and are cultivated in a cell culture.

The cultivated cells are transplanted back into the cartilage defect zone during a second intervention.

The defective tissue has previously been removed from the cartilage defect zone, for which purposes a device mentioned at the outset is used for the punching operation.

In this so-called defect preparation, the edges have to be as smooth as possible and at right angles, specifically such that the prepared defect edges are delimited on all sides by stable cartilage. The defect base ought to reach as far as the subchondral bone. A cartilage punch corresponding to the size of the defect is applied and firmly pressed in. The contour of the circumferential cutting edge corresponds approximately to the contour of the tissue area to be punched out; this area can be circular, oval or of another shape. By means of a sharp spoon or a ring curette, the defective tissue area is scraped off (debrided) as far as the osteochondral zone.

The biopsy specimen produced beforehand is then transplanted back into the area that has been prepared in this way.

The known punches that are used have a continuous circumferential cutting edge that lies in one plane. The punches are usually made up of a hollow body, for example a tube, whose end edge extending approximately perpendicular to the longitudinal axis is ground down to form a cutting edge.

In practical use, it has now been found that optimal defect preparation is not possible with blades of this kind, because in most cases the bone surface from which the tissue area is to be separated is not even. As has already been mentioned, such defects occur particularly in the area of the knee joint, where the bone surface is strongly curved.

When a bone punch with a flat blade line is driven into a curved bone surface, this inevitably means that only some tissue areas can be incised to the optimal depth, while others cannot.

Remedial measures, such as tilting the punch back and forward, does not provide the desired smooth edges prepared at right angles.

It is therefore an object of the present invention to remedy this situation and to develop a device of the type mentioned in the introduction such that optimal defect preparation is possible.

SUMMARY OF THE INVENTION

According to the invention, the object is achieved by the fact that the blade of the device for punching out tissue areas is composed of a plurality of blade segments that are each movable in an axial direction counter to the force of an elastic element.

These measures have the advantage that, by dividing the blade into individual blade segments, and by these each being acted on by the force of an elastic element, these blade segments can penetrate into the cartilage tissue independently of the other blade segments. If the bone area is curved in a dome shape, and if the blade is applied in the area of the dome, the corresponding blade segments can penetrate deeper into the cartilage tissue in those areas where the dome slopes down slightly farther.

In other words, as far as their depth of penetration is concerned, the individual blade segments can adapt to the contour of the underlying (subchondral) bone surface. A punch line is thus generated that adapts automatically to the respective substructure of the bone. Since the blade segments are movable in the axial direction, a cutting edge is obtained that is reliably smooth and suitably at right angles. Through the choice of the number of blade segments, it is possible to create a blade line more or less adapted to the undulated substructure or bone surface. If the bone base is only gently undulated or curved, 5 or 10 blade segments may suffice for a blade line length of 10 cm for example, while more segments, for example up to 20 blade segments, can be provided for a strongly undulated surface.

The blade line is thus optimally adapted to the anatomy of the bone surface, with the result that an optimal preparation of the defect is possible. The subsequent scraping off of the punched-out tissue area from the bone base is made much easier than in cases when some areas of the tissue are not incised or punched to the optimal depth, on account of the undulating geometry of the substructure of the bone.

The elastic element can be made from an elastically deformable material.

In one embodiment, the elastic element is designed as a spring, and the blade segment can be moved counter to the force of said spring.

In another embodiment of the invention, the blade segments are received in a guide.

This measure has the advantage that the blade segments are guided exactly in their axial reciprocating movement, so that particularly smooth and right-angled cuts can be made.

In another embodiment of the invention, a blade segment can be acted on by the elastic element or spring in such a way that it can be pressed out past the distal edge of the guide.

This measure has the advantage that a variable length section is present which at the same time also defines the maximum depth of penetration of the blade into tissue.

This not only permits variable adaptation of the blade line to the contour of the bone surface from which the cartilage tissue is to be separated, but also limits the maximum depth of penetration, so as to rule out the possibility of the bone being damaged by inadvertently pushing the blade of the punch in too far.

In another embodiment of the invention, the guide has an outer wall and, arranged radially inward from the latter, an inner wall, between which walls the blade segments are received.

This measure has the advantage that the blade segments are guided in the radial direction by the wall and are also protected from being damaged. It is thus also possible for the individual blade segments to be arranged next to one another as Individual segments, since they are held and guided by the inner and outer walls and are additionally guided in the circumferential direction by an adjacent blade segment.

This permits particularly safe handling.

In another embodiment of the invention, the device is designed as a hollow body that is divided into at least two hollow body segments, at least one hollow body segment being axially displaceable relative to another.

This measure has the considerable advantage that the punching operation can first be carried out, and one of the two hollow body segments can then be withdrawn axially, as a result of which sufficient space is created for scraping off the tissue from the bone with the spoon. Some of the blades are still pressed into the tissue, as a result of which this area serves as a support or abutment for the spoon, so that this scraping can take place such that the edges are not damaged by this scraping process.

This results in particularly exact and smooth edges in the punched-out area.

In another embodiment of the invention, the hollow body segment comprises the guide and the blade segments guided by the latter.

The hollow body is thus composed of different blade units, of which at least one can be axially withdrawn as a complete structural unit, so that the operating surgeon has sufficient space to scrape off material with the spoon.

In another embodiment of the invention, the blade segments of a hollow body segment are axially movable together in the guide.

This measure has the considerable advantage that the blade segments of the hollow body segment that is withdrawn can be drawn back axially even further, so as to disappear completely in the guide, particularly between the inner and outer walls. This ensures that, when scraping out the tissue area, the operating surgeon cannot accidentally injure himself on the blades of the axially retracted hollow body segment.

In another embodiment of the invention, the springs of the blade segments are supported on a common support that is axially displaceable between the walls.

This measure has the advantage that the blade segments, either of the entire hollow body or only of the axially movable hollow body segment, can be moved to and fro in a single displacement by means of the aforementioned movement, for example in order to be drawn back into the guide for protection.

This additionally has the advantage that during storage, or during preparation for an operation, the blades are initially set back behind the distal edge of the device and are pushed out only at the time of the actual punching procedure.

This protects the sometimes very thin blade segments from damage and at the same time protects the operator from injury when preparing the operating equipment.

In another embodiment, the device comprises a spoon for removing the punched-out area of tissue.

This measure has the advantage that the geometry of the spoon can in each case be adapted to the geometry of the hollow body, so that this makes a further contribution to optimal removal of tissue.

It will be appreciated that the aforementioned features and those still to be explained below can be used not only in the respectively cited combination, but also in other combinations or singly, without departing from the scope of the present invention.

BRIEF DESCRIPTION OF THE DRAWINGS

The invention is described and explained in greater detail below on the basis of a selected illustrative embodiment and with reference to the attached drawings, in which.

DETAILED DESCRIPTION OF PREFERRED EMBODIMENTS

In FIGS. 1 to 6, a device for punching out tissue areas is designated in its entirety by reference number 10.

Figure 1:
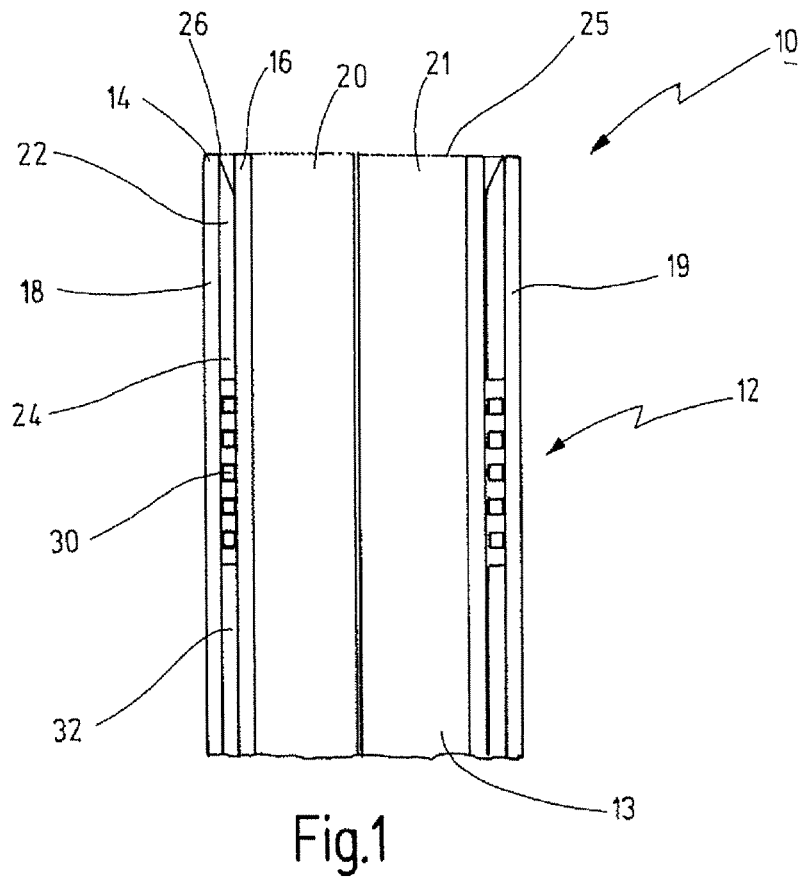
FIG. 1 shows a longitudinal section through a distal end portion of a punching device according to the invention.
Figure 2:
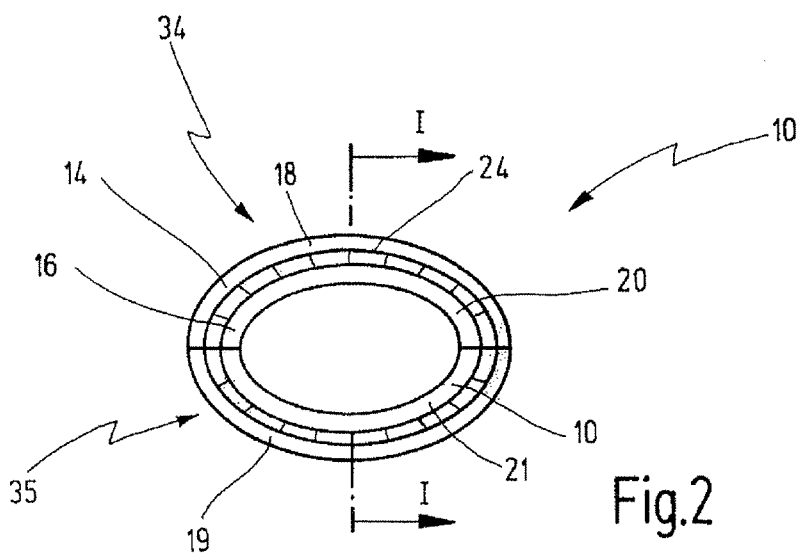
FIG. 2 shows a plan view of the distal end area of the device from FIG. 1, illustrating its oval contour.

In its distal end area, the device 10 has a hollow cylindrical body, shown in FIG. 1, with an elliptical cross section, as can be seen from the sectional view in FIG. 2.

The hollow cylindrical body 12 has an outer wall 14 and, arranged radially inward from the latter, an inner wall 16.

The outer wall 14 is composed of two elliptical half-shells 18 and 19, and the inner wall 16 is composed of corresponding half-shells 20 and 21. A blade 22 is received in the gap between outer wall 14 and inner wall 16.

The assembly composed of outer wall 14 and inner wall 16 thus serves as a guide for the blade 22.

Figure 3:
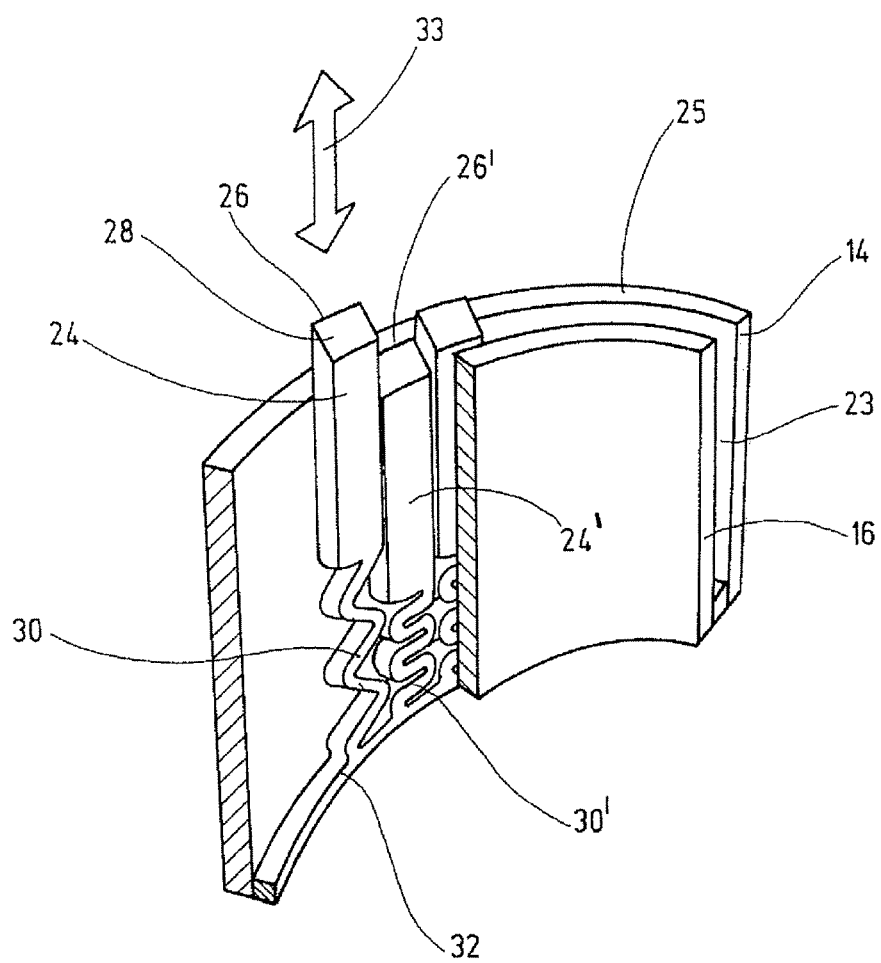
FIG. 3 shows a greatly enlarged perspective and partially cut away view of a circumferential portion of the distal end area of the device from FIG. 1.

As can be seen in particular from FIG. 3, the blade 22 is composed of a multiplicity of blade segments 24, 24'.

Each blade segment 24 is composed of a hollow cylinder segment that is beveled at the distal end with a downward slope, as viewed from radially outward to radially inward. The higher edge of the bevel 28 thus forms a cutting edge 26.

The blade segments 24 are designed and arranged in such a way that they completely fill the space between the outer wall 14 and the inner wall 16 in the circumferential direction, the blade segments 24, 24' being arranged lying next to one another, but in such a way that they can move in the axial direction, as is indicated by the double arrow 33. It will be seen from the plan view in FIG. 2 that twenty blade segments 24 are provided in total.

At its end remote from the cutting edge 26, each blade segment 24 is connected to an elastic element in the form of a spring 30, which is supported on a support 32.

Each spring 30 is pretensioned in such a way that it tends to press a blade segment 24 out past a distal edge 25 of the hollow cylindrical body 12.

In FIG. 3, the blade segment 24 is shown in its position of maximum extraction past the distal edge 25.

The adjacent blade segment 24 is driven in so far, or moved or pressed proximally in the axial direction, such that its cutting edge 26' is flush with the distal edge 25.

The blade segment lying farther to the right of this in the illustration in FIG. 3 is shown in an intermediate position between the two positions of the blade segments 24 and 24'.

In the embodiment in FIG. 3, the spring 30 is integrally connected at one end to the support 32, which again has a half-shell shape, and it is integrally connected at the other end to the blade segment 24. This geometry can be obtained directly from solid material by means of a laser cutting operation.

It is also possible to place a separate spring between the blade segment 24 and the support 32, in which case corresponding guides have to be provided for the springs.

Figure 4:
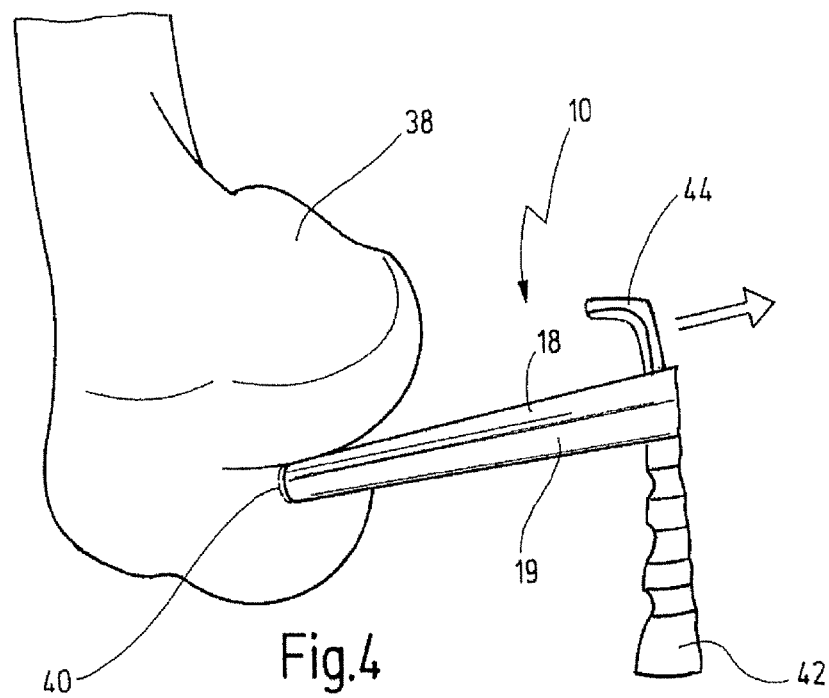
FIG. 4 shows a highly schematic representation of the use of the device in a defect preparation on a knee joint.
Figure 5:
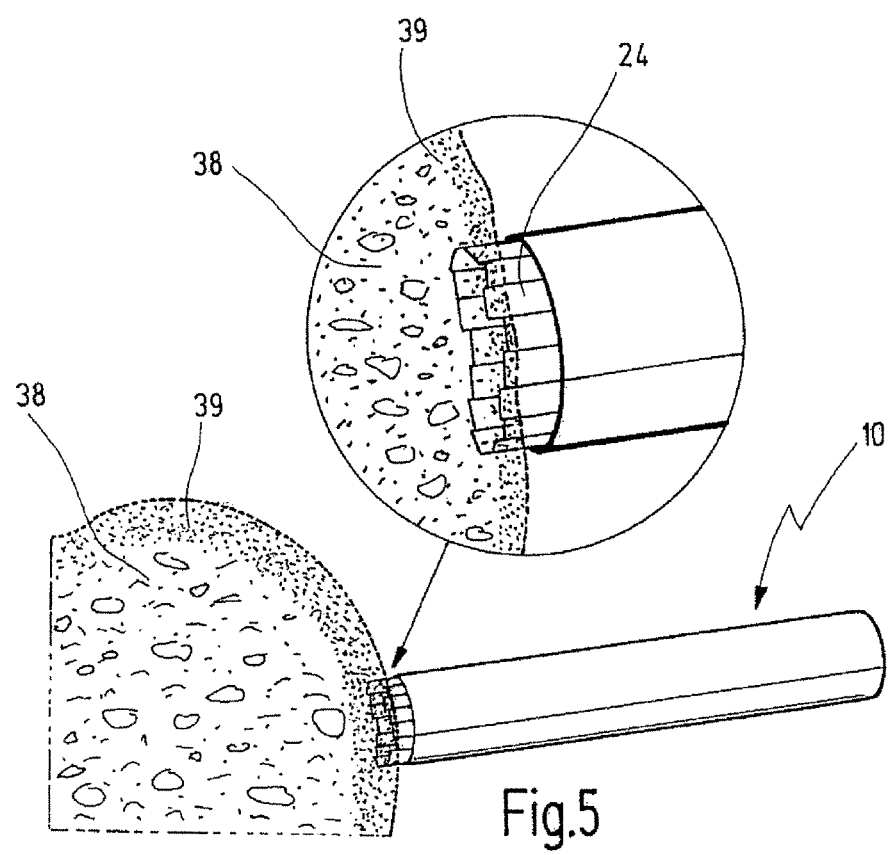
FIG. 5 shows a greatly enlarged detail of the defect preparation, and the area bordered by a circle shows a still further enlarged representation of the blade segments penetrating into the hyaline articular cartilage.
Figure 6:
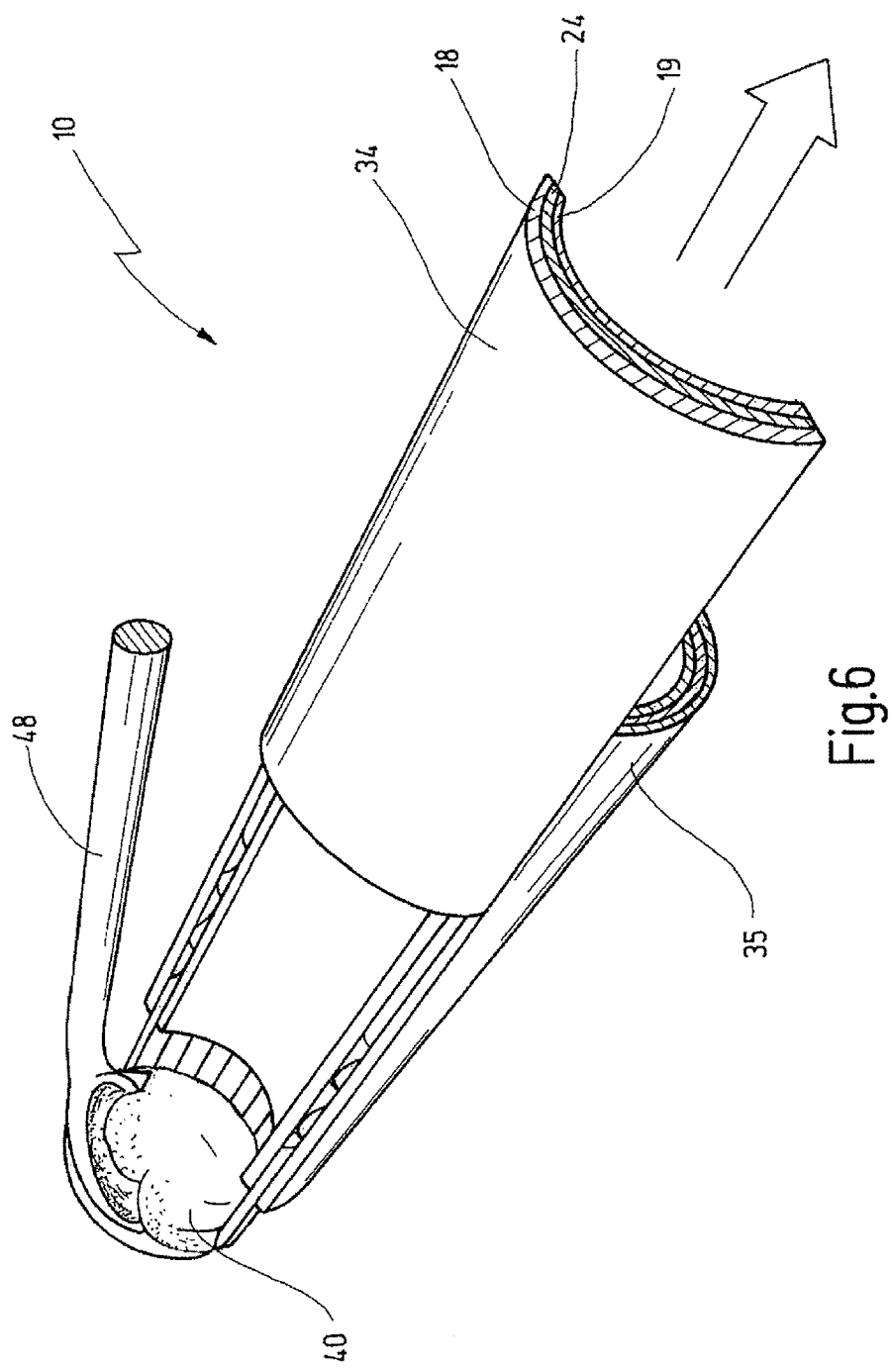
FIG. 6 shows a perspective partial view of the device according to the invention from FIG. 5, with a hollow body element axially retracted so that the punched-out area of cartilage can be removed using a spoon.

FIGS. 4 to 6 show a manipulation of the device 10, specifically the removal of a tissue area 40 of cartilage tissue 39 that covers a bone 38, in this case the human femur, for example.

As was mentioned in the introduction, the tissue area 40 to be removed is a defect area that is to be replaced by other tissue.

The device 10 according to the invention is used here as a tissue punch in order to be able to remove this tissue area 40.

As can be seen from FIG. 4, the device 10 has a grip 42 that protrudes laterally from the hollow cylindrical body 12.

This is just one design example. If the operation is carried out by arthroscopy, that is to say through a trocar, the hollow cylindrical body 12 is accordingly longer, and a grip or a scissor-like maneuvering element is arranged at a greater distance from the removal site.

However, this is a question of the particular design and of the type of intervention, that is to say whether it is a minimally invasive operation or an operation performed on an exposed knee joint.

The handgrip 42 is in this case mounted on the outside of the half-shell 19.

On the opposite side, a bracket 44 protrudes from the other half-shell 18, the purpose of which bracket 44 will be explained later in connection with FIG. 6.

For the procedure referred to as a defect preparation, a device 10 with the desired geometry is chosen, in this case the geometry shown in FIG. 2, that is to say with an oval cross section. The cutting edge 26, which is composed of the respective cutting edges 26 of the blade segments 24, encloses an area of approximately 10 cm². As can be seen in particular from FIG. 5 and from the larger area enclosed by a circle, the device 10 is placed with its distal end on the cartilage tissue 39 that surrounds the bone 38, specifically in the area of the defect, i.e. of the tissue area 40.

The device 10 is pressed into the cartilage tissue 39, the individual blade segments 24 penetrating to the extent permitted by the surface of the bone 38, i.e. the contour of the cutting edge of all the blade segments 24 adapts to the correspondingly curved contour of the bone 38.

The optimal depth of penetration is thus achieved in the area of each individual blade segment 24, and, at the same time, a defect preparation is obtained in which the edges are very smooth and at right angles.

The punched-out tissue area 40 is removed from the bone 38 using a spoon 48 (shown in FIG. 6) with sharp edges, or a curette.

The tissue area is scraped off as far as the osteochondral zone.

To make this procedure easier, it is proposed that the hollow body segment 34, as can be seen in FIG. 6, can be pulled off proximally in the axial direction. The bracket 44 makes this procedure easier.

The hollow body segment 34 is thus composed of the half-shell 19 of the inner wall and the half-shell 18 of the outer wall, and of the corresponding blade segments 24 received between said walls.

As has been explained in connection with FIG. 3, the springs 30 are pretensioned in such a way that they press the blade segments 24, 24' out past the distal edge 25.

Since all the springs 30 of a hollow body segment are supported on a common support 32, this opens up the possibility of drawing this support 32 further in the proximal direction between the half-shells 18 and 19, so that the protruding parts of the blade segments 24 are drawn in between these edge areas, that is to say no longer extend past the distal edge 25. This ensures that the operating surgeon does not injure himself while maneuvering the spoon 48.

This maneuvering involves the tissue area 40 being completely scraped off from the bone and removed using the spoon 48, as shown in FIG. 6.

Depending on the operating technique, an endogenous periosteal flap, for example one taken from the proximal tibia, is then fitted into the prepared defect area, or a suitably cultured biopsy is used.

What is claimed is:

1. A device for punching out tissue areas from bone, comprising:
   a blade body having a closed circumferential cutting edge configured to surround a tissue area that is to be punched out,
   wherein said blade body is composed of a plurality of separate blade segments, said separate blade segments being arranged lying adjacent to one another resulting in said blade body and said closed circumferential cutting edge,
   each of said separate blade segments being movable in an axial direction counter to a force of a respective elastic element.

2. The device of claim 1, wherein said respective elastic element is designed as a spring.

3. The device of claim 1, wherein said separate blade segments are received in a guide.

4. The device of claim 3, wherein said guide has an outer wall and, arranged radially inward from the latter, an inner wall, said separate blade segments being received between said inner and said outer wall.

5. The device of claim 3, wherein said device is designed as a hollow body that is divided into at least two hollow body segments, at least one of said at least two hollow body segments being axially displaceable relative to another one.

6. The device of claim 5, wherein said hollow body segments comprise said guide and said separate blade segments, guided by said guide.

7. The device of claim 6, wherein said separate blade segments of one hollow body segment are axially movable together in said guide.

8. The device of claim 7, wherein said respective elastic element of each of said separate blade elements is supported on a common support being axially displaceable between said inner and said outer wall.

9. The device of claim 8, wherein said respective elastic element is designed as a spring.

10. The device of claim 1, wherein each of said separate blade segments can be acted on by said respective elastic element in such a way that it can be pressed out by an axial length section past a distal edge of said device.

11. The device of claim 1, wherein a spoon is provided for removing said tissue area that has been punched out by said blade body.

\* \* \* \* \*